(12) United States Patent
Choi et al.

(10) Patent No.: US 10,420,487 B1
(45) Date of Patent: Sep. 24, 2019

(54) SYSTEM OF MONITORING SPORTS ACTIVITY AND ACCIDENT AND METHOD THEREOF

(71) Applicant: HWASUNG, Gangneung-si, Gangwon-do (KR)

(72) Inventors: Jongdoo Choi, Gangneung-si (KR); Geonha Lee, Samcheok-si (KR); Kihyun Lee, Gangneung-si (KR); Jongseok Choi, Gangneung-si (KR)

(73) Assignee: HWASUNG, Gangneung-si, Gangwon-Do (KR)

( * ) Notice: Subject to any disclaimer, the term of this patent is extended or adjusted under 35 U.S.C. 154(b) by 0 days.

(21) Appl. No.: 15/996,747

(22) Filed: Jun. 4, 2018

(30) Foreign Application Priority Data

Apr. 19, 2018 (KR) .................. 10-2018-0045581

(51) Int. Cl.
*A61B 5/00* (2006.01)
*A61B 5/11* (2006.01)
(Continued)

(52) U.S. Cl.
CPC .......... *A61B 5/1118* (2013.01); *A61B 5/0022* (2013.01); *A61B 5/0205* (2013.01); *A61B 5/6801* (2013.01); *A61B 5/7225* (2013.01); *A61B 5/7275* (2013.01); *A61B 5/7282* (2013.01); *A61B 5/746* (2013.01); (Continued)

(58) Field of Classification Search
CPC ..... A61B 5/1118; A61B 5/7275; A61B 5/486; A61B 5/112; A61B 5/1121; A61B 5/0022; A61B 5/0205; A61B 5/6801; A61B 5/7225; A61B 5/746; A61B 5/7475; A61B 5/7282; A61B 5/02438; A61B 2503/10; A61B 2562/029; A61B 2562/0219; A61B 2562/0223; A61B 2562/0271; G01C 22/00
See application file for complete search history.

(56) References Cited

U.S. PATENT DOCUMENTS 8,164,472 B2 * 4/2012 Stewart ............... H04N 7/18 280/11
8,482,417 B2 * 7/2013 Stewart ............... H04N 7/18 280/11
(Continued)

FOREIGN PATENT DOCUMENTS

KR 10-1176106 8/2012
KR 10-1676848 11/2016
(Continued)

*Primary Examiner* — Hoi C Lau
(74) *Attorney, Agent, or Firm* — Kile Park Reed & Houtteman PLLC

(57) ABSTRACT

The present invention relates to a sports activity and accident risk monitoring system and a method thereof. The system includes a wearable sensing device that is as worn by a user and is capable of sensing an activity state of the user; a terminal capable of processing activity information in conjunction with the wearable sensing device; and a server that is connected to the terminal through a network, grasps a sports activity pattern, personal data for each item, and whether or not an accident occurs by receiving, processing, and analyzing the activity information of the user, and transmits a feedback signal to the terminal.

5 Claims, 12 Drawing Sheets
(9 of 12 Drawing Sheet(s) Filed in Color)

(51) Int. Cl.
*G06F 1/16* (2006.01)
*G01C 22/00* (2006.01)
*G06N 20/00* (2019.01)
*A61B 5/024* (2006.01)
*G06N 3/04* (2006.01)
*A61B 5/0205* (2006.01)

(52) U.S. Cl.
CPC ............ *A61B 5/7475* (2013.01); *G01C 22/00* (2013.01); *A61B 5/02438* (2013.01); *A61B 2503/10* (2013.01); *A61B 2562/029* (2013.01); *A61B 2562/0219* (2013.01); *A61B 2562/0223* (2013.01); *A61B 2562/0271* (2013.01); *G06F 1/163* (2013.01); *G06N 3/04* (2013.01); *G06N 20/00* (2019.01)

(56) References Cited

U.S. PATENT DOCUMENTS

| | | | | |
|---|---|---|---|---|
| 2011/0270135 A1* | 11/2011 | Dooley | ............... | A61B 5/1121 600/595 |
| 2014/0085050 A1* | 3/2014 | Luna | ................. | G07C 9/00087 340/5.82 |
| 2014/0089672 A1* | 3/2014 | Luna | .................... | H04L 9/3231 713/186 |
| 2014/0089673 A1* | 3/2014 | Luna | ................. | H04L 63/0861 713/186 |
| 2015/0019135 A1* | 1/2015 | Kacyvenski | ......... | A61B 5/0488 702/19 |
| 2015/0038806 A1* | 2/2015 | Kaleal, III | .......... | A61B 5/4872 600/301 |
| 2015/0048926 A1* | 2/2015 | Vincent | .............. | G07C 9/00111 340/5.61 |
| 2015/0099946 A1* | 4/2015 | Sahin | ...................... | A61B 5/16 600/301 |
| 2015/0223731 A1* | 8/2015 | Sahin | ...................... | A61B 5/16 600/301 |
| 2015/0324698 A1* | 11/2015 | Karaoguz | ............... | H04L 67/22 706/46 |
| 2016/0027278 A1* | 1/2016 | McIntosh | ........... | G08B 21/0423 715/741 |
| 2016/0086500 A1* | 3/2016 | Kaleal, III | ............. | G06T 19/00 434/257 |
| 2016/0125348 A1* | 5/2016 | Dyer | ................ | G06Q 10/06398 705/7.42 |
| 2016/0171864 A1* | 6/2016 | Ciaramelletti | ......... | A42B 3/046 340/539.12 |
| 2016/0210838 A1* | 7/2016 | Yan | ...................... | G08B 21/043 |
| 2016/0232807 A1* | 8/2016 | Ghaffari | ............... | G09B 19/00 |
| 2016/0345865 A1* | 12/2016 | Agrawal | ............... | A61B 5/1036 |
| 2017/0084070 A1* | 3/2017 | Chamdani | ............... | G06T 13/40 |
| 2017/0147788 A1 | 5/2017 | Ohnemus et al. | | |
| 2017/0157482 A1 | 6/2017 | DeCarlo | | |
| 2017/0182360 A1* | 6/2017 | Chang | ...................... | G06F 7/02 |
| 2017/0188894 A1* | 7/2017 | Chang | .................... | G06F 19/00 |
| 2017/0344919 A1* | 11/2017 | Chang | ................ | G06Q 10/0633 |
| 2017/0355377 A1* | 12/2017 | Vijaya Kumar | ...... | B60W 40/08 |
| 2018/0125423 A1* | 5/2018 | Chang | .................. | A61B 5/1114 |
| 2018/0133551 A1* | 5/2018 | Chang | ................... | A63B 24/0062 |
| 2018/0153430 A1* | 6/2018 | Ang | .................. | A61B 5/04001 |

FOREIGN PATENT DOCUMENTS

| | | |
|---|---|---|
| KR | 10-2016-0143012 | 12/2016 |
| KR | 10-1764227 | 8/2017 |

* cited by examiner

SYSTEM OF MONITORING SPORTS ACTIVITY AND ACCIDENT AND METHOD THEREOF

TECHNICAL FIELD

The present invention relates to a system of monitoring sports activity and accident and a method thereof, and particularly, to a technology that can monitor sports activity patterns, personal data for each item, and accident and can warn an accident risk by collecting sports activity information using a wearable device and transmitting the sports activity information to a server through a personal terminal to analyze using a machine learning technique.

BACKGROUND ART

With recent increases in income levels, the number of people who enjoy various sports such as jogging, mountain climbing, cycling, snowboarding, and motorcycles is increasing due to increased leisure time.

As the ability to experience and enjoy sports and leisure simply increases, so-called enthusiasts are being interested in their current level and development.

In addition, with a rapid development of a smart phone, a tablet PC, and a mobile application in recent years, various hardware and software services associated with user sports activities are rapidly spreading.

Hence, according to this tendency, the sports activity is not merely recorded but recorded as data, and thereby, the desire to withdraw and monitor the sports activity is increasing.

The activity information recording/monitoring service not only makes a goal consciousness of a user clear, but also can contribute to the improvement of his/her own ability and skill on an objective basis.

For this reason, it is necessary to invent a system that not only simply records and browses the activity information data but also transmits the activity information data as reliable data, stores the activity information data in the service server to classify, and suggests the analysis results optimized for individual activity tendency through machine learning and an analysis algorithm.

In addition, since, while being generalized, spreading the social network service (SNS) and users can be shared by acquaintances or unspecified persons instead of simply monitoring personal information, data collection and an algorithm for analysis can also continue to evolve.

However, there are problems in the related art in which a situation can occur where a person enjoys himself/herself or enjoys separately from a group thereof in sports activities and, when there is an unexpected accident, recognition of accident or discovery of victim is delayed and thereby rescue golden time can be missed.

In addition, it is difficult to grasp the degree of exercise ability of a person who exercises by setting the exercise time or a posture only by subjective judgment, feeling, and sense thereof at the time of sports activity, and it is difficult to improve the exercise performance because of difficulty to grasp a wrong habit or weakness of the person during exercise, and moreover, there is a problem in which there is a limit in predicting the accident.

Patent Document 1: Patent No. 1016768480000 (Title: Smart Safety Helmet and Method, Safety Management System Using the Same, and Method Thereof).

Patent Document 2: Patent No. 1011761060000 (Title: Bluetooth Bicycle Helmet).

Patent Document 3: Patent No. 1017642270000 (Title: Sports Prediction Analysis Interface System and Method Using Big Data-based Data Mining Technique).

DETAILED DESCRIPTION OF THE INVENTION

Technical Problem

An object of the present invention is to provide a system and method that can monitor sports activity patterns, personal data for each item, and accident and can warn an accident risk by collecting sports activity information using a wearable device and transmitting the sports activity information to a server through a personal terminal to analyze using a machine learning technique.

Technical Solution

According to an embodiment of the present invention, a sports activity monitoring system includes a wearable sensing device that is as worn by a user and is capable of sensing an activity state of the user; a terminal capable of processing activity information in conjunction with the wearable sensing device; and a server that is connected to the terminal through a network, grasps a sports activity pattern, personal data for each item, and whether or not an accident occurs by receiving, processing, and analyzing the activity information of the user, and transmits a feedback signal to the terminal.

According to another embodiment, a sports activity monitoring method includes transmitting activity information data from a wearable sensing device which is worn by a user; inputting user information and a menu through a terminal, processing the transmitted activity information data, and transmitting user information, activity information and item information to a server; setting an activity type, an activity history, the amount of activity, trend analysis, and a goal value by classifying the received activity information data by user, sports activity item, and period using the server and performing an arithmetic operation of the data using artificial intelligence; determining whether or not there is an accident risk by analyzing the activity information data and comparing the analyzed data with a reference value using the server; and transmitting an analyzed activity state and presence or absence of the accident risk to the terminal to inform the user using the server.

Advantageous Effects of the Invention

According to an embodiment of the present invention, a sports activity monitoring system and a sports activity monitoring method have the following advantages.

First, the system and method collect sports activity information of a user from a wearable sensing device worn by the user's body and an apparatus, can monitor and analyze the sports activity information through a smart phone and an application, and helps the user to improve his/her sports activity and skill, and thus, it is possible to make more scientific and systematic sports activities.

Second, more accurate measurement can be made by adding calibration as analysis of sensing information is accumulated through machine learning.

Third, a machine learning technology can be applied to data separately accumulated in the process of analyzing sensing information to provide personal customized information, and it is possible to provide an activity information monitoring service that is improved since the more you use, the higher the accuracy is.

Fourth, Patterns of accidents and risk situations that are different from usual can be detected in the process and results of information analysis, and thereby, it is possible to respond appropriately when a user faces accidents and dangerous situations that may be caused during physical activities, and to warn an accident risk in advance.

DESCRIPTION OF THE DRAWINGS

The patent or application file contains at least one drawing executed in color. Copies of this patent or patent application publication with color drawings will be provided by the Office upon request and payment of the necessary fee.

MODE OF THE INVENTION

Hereinafter, a system and a method for monitoring sports activity and accident detection according to an embodiment of the present invention will be described in detail with reference to the accompanying drawings.

Figure 1:
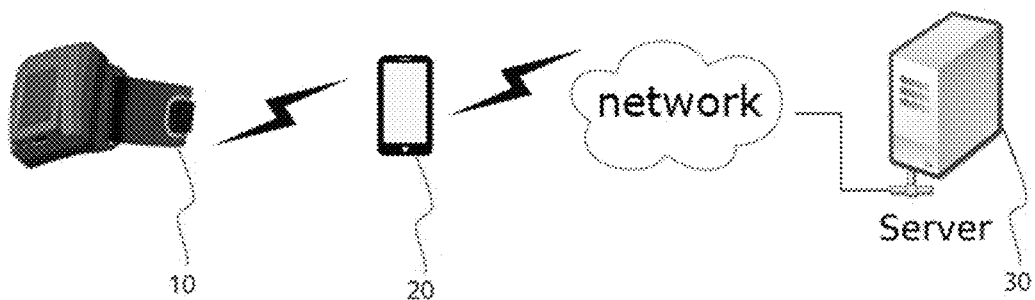
FIG. 1 is an overall configuration diagram of a sports activity information monitoring system according to an embodiment of the present invention.
Figure 2:
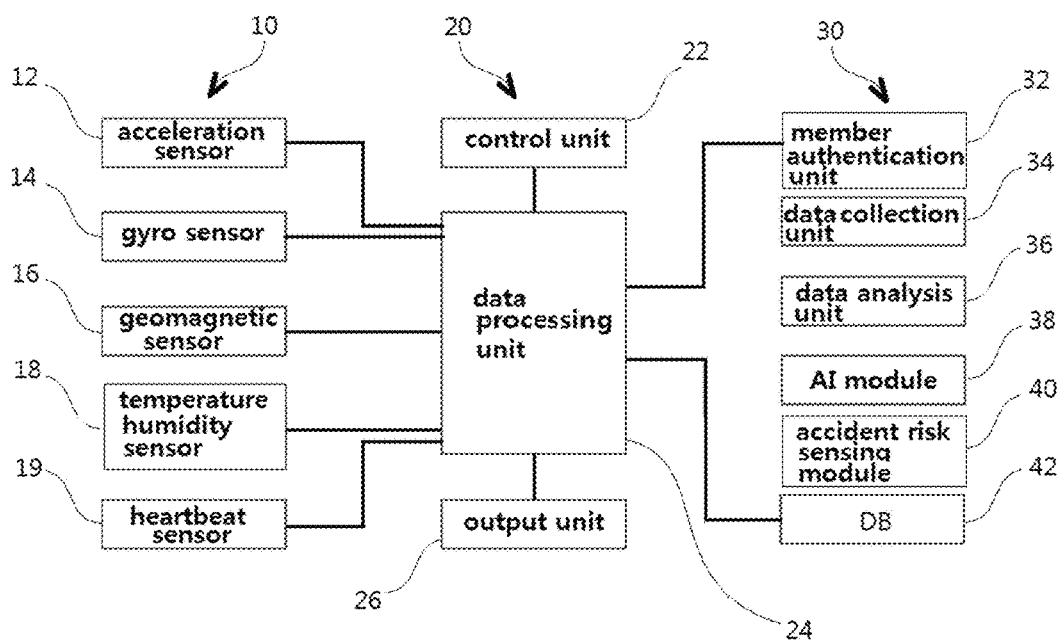
FIG. 2 is an internal block diagram of the sports activity information monitoring system illustrated in FIG. 1.
Figure 3:
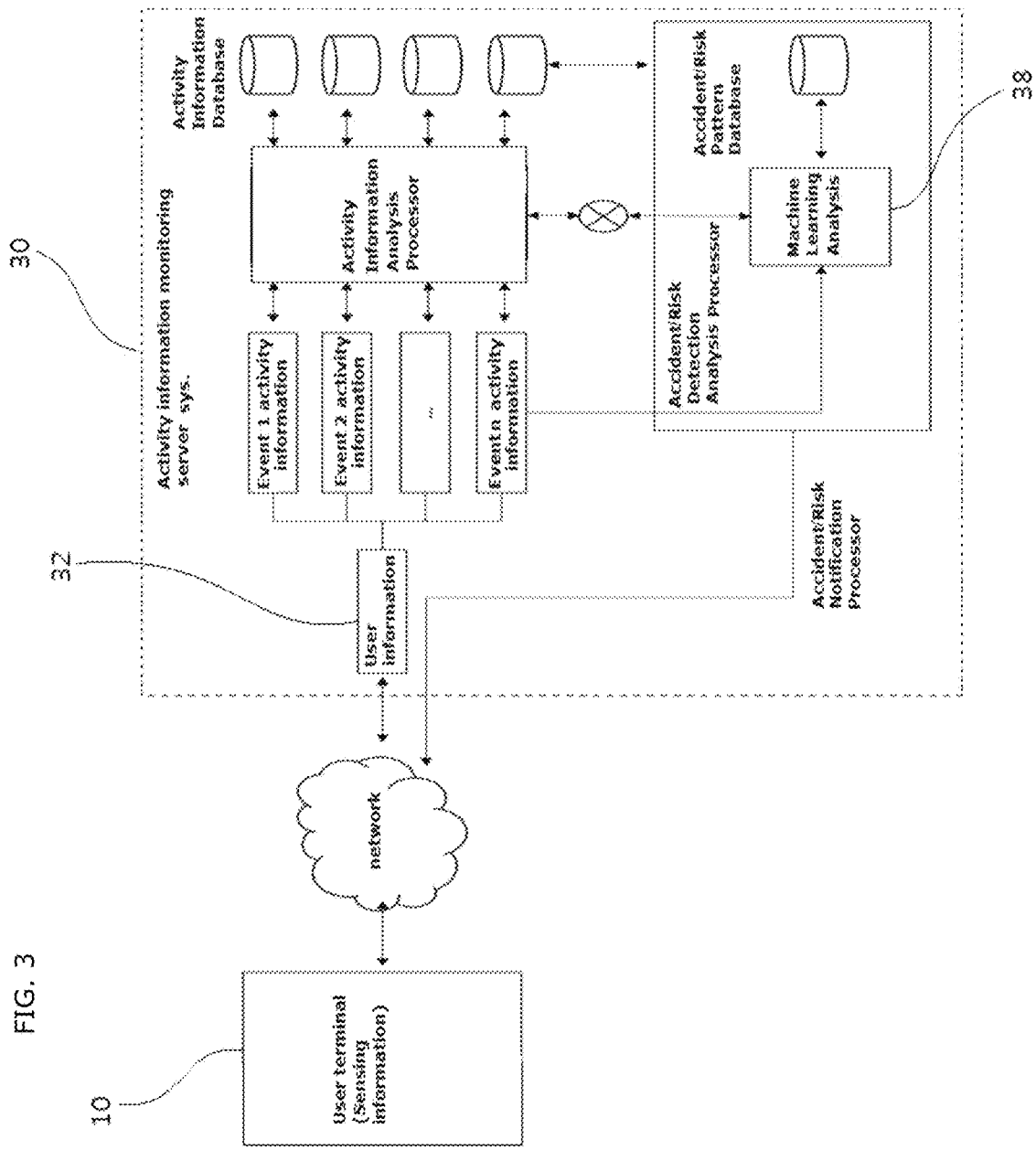
FIG. 3 is a conceptual diagram illustrating performance of the sports activity information monitoring and the accident detection analysis processing illustrated in FIG. 1.
Figure 4:
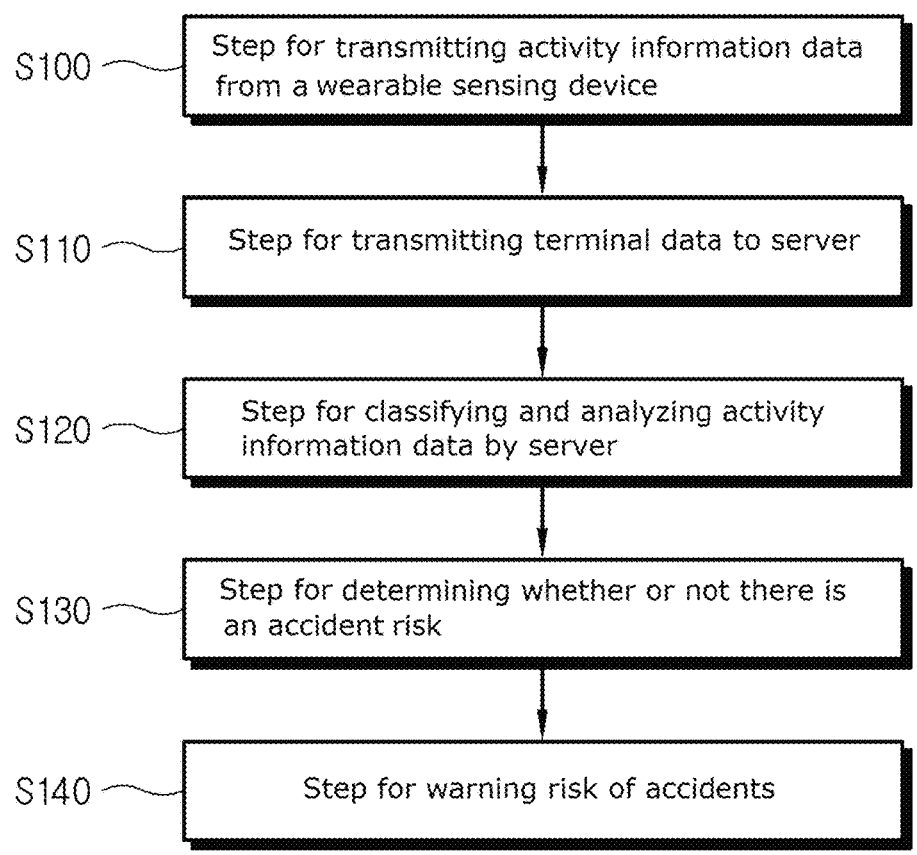
FIG. 4 is a flowchart illustrating a sports activity information monitoring method according to another embodiment of the present invention.

As illustrated in FIGS. 1 and 3, a sports activity monitoring system proposed by the present invention includes a wearable sensing device 10 capable of sensing activity information as worn by a user, a terminal 20 capable of processing the activity information in conjunction with the wearable sensing device 10, and a server 30 that grasps a sports activity pattern, personal data for each item, and whether or not an accident occurs, and transmits a feedback signal to the terminal 20 by transmitting and receiving signals to and from the terminal 20 through a network to receive and analyze activity information of a user.

In the sports activity monitoring system, the wearable sensing device 10 can sense a current activity state as worn on the body such as an arm or a leg of a user.

More specifically, the wearable sensing device 10 includes an acceleration sensor 12, a gyro sensor 14, a geomagnetic sensor 16, a temperature and humidity sensor 18, and a heartbeat sensor 19.

An acceleration value measured by the acceleration sensor 12 is transmitted to the terminal 20 and processed by a data processing unit 24.

The gyro sensor 14 is capable of measuring angular speeds of three axes of X, Y and Z. Since the gyro sensor 14 is capable of detecting a rotation angle and an inclination of a rotating object, the gyro sensor 14 is capable of sensing movement of an object in association with the acceleration sensor 12 that measures an acceleration of the object.

Accordingly, an angular velocity value measured by the gyro sensor 14 is transmitted to the terminal 20 and processed by the data processing unit 24.

The geomagnetic sensor 16 senses a geomagnetism using the Hall effect, a magnetic force measured by the geomagnetic sensor 16 is transmitted to the terminal 20 and processed by the data processing unit 24.

The temperature and humidity sensor 18 is formed by integrating a temperature sensor with a humidity sensor, and the measured temperature and humidity are transmitted to the terminal 20 and processed by the data processing unit 24.

The heartbeat sensor 19 is capable of measuring a heartbeat of a user. Then, the measured heartbeat is transmitted to the terminal 20 and processed by the data processing unit 24.

The data measured by the wearable sensing device 10 is transmitted to the terminal 20 to be processed.

The terminal 20 means a communication device capable of transmitting and receiving signals to and from the wearable sensing device 10 and the server 30 in a wired and wireless manner and capable of processing data. For example, the terminal means a mobile communication device such as a smart phone or a tablet PC. In addition, the terminal 20 has an application installed therein, thereby, being capable of processing activity data transmitted from the wearable sensing device 10 to transmit the processed data to the server 30.

The terminal 20 includes a data processing unit 24, a control unit 22, and an output unit 26.

The data processing unit 24 converts real-time activity data, user information, location information, history information, a sensing period, and related information which are received from the wearable sensing device 10 into a predetermined protocol form, filters the data, and transmits the data to the server 30.

The control unit 22 processes a command input by a user through a screen of the terminal 20 or the like in conjunction with the data processing unit 24, or receives or transmits data from or to the wearable sensing device 10 and the server 30.

The control unit 22 receives and processes data, and outputs the processed data, like a microprocessor.

The output unit 26 transmits the data processed by the data processing unit 24 to each electronic element in the terminal 20 or transmits the data to the server 30. Various transmission methods are available, for example, 2.4 GHz Bluetooth communication is available. This process is continuously performed by a user command during sensing.

The terminal 20 processes the command input by a user or processes the data received from the wearable sensing device 10 and transmits the processed data to the server 30.

The terminal 20 activates a related application installed, thereby, popping up an input window on the screen and receiving information of the user.

For example, the terminal receives additional information on login information, his/her main sports activities, designated activity items, location information, a sensing apparatus, and the like.

In addition, by displaying a menu on the screen of the terminal 20, the user is able to select the menu by touching or the like to process the menu.

Figure 5:
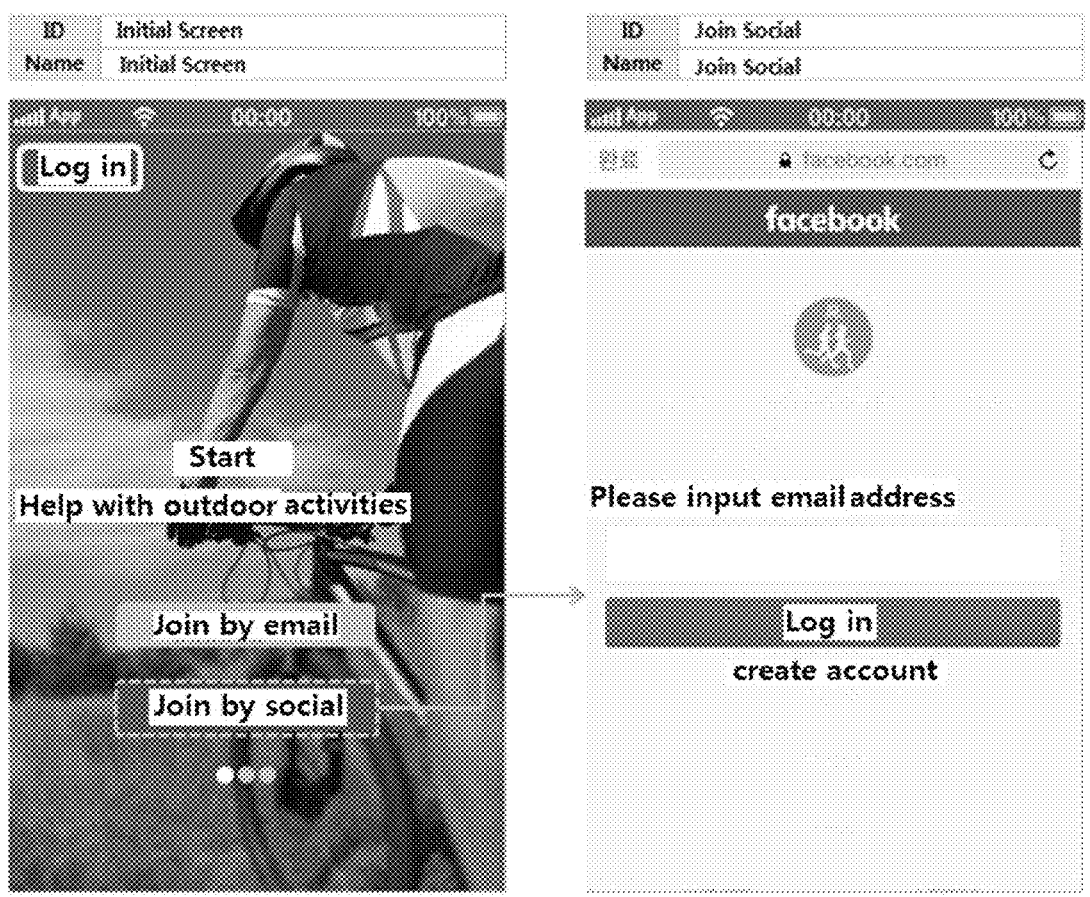
FIGS. 5 to 12 are diagrams illustrating menu forms displayed on a screen of a terminal illustrated in FIG. 1.
Figure 6:
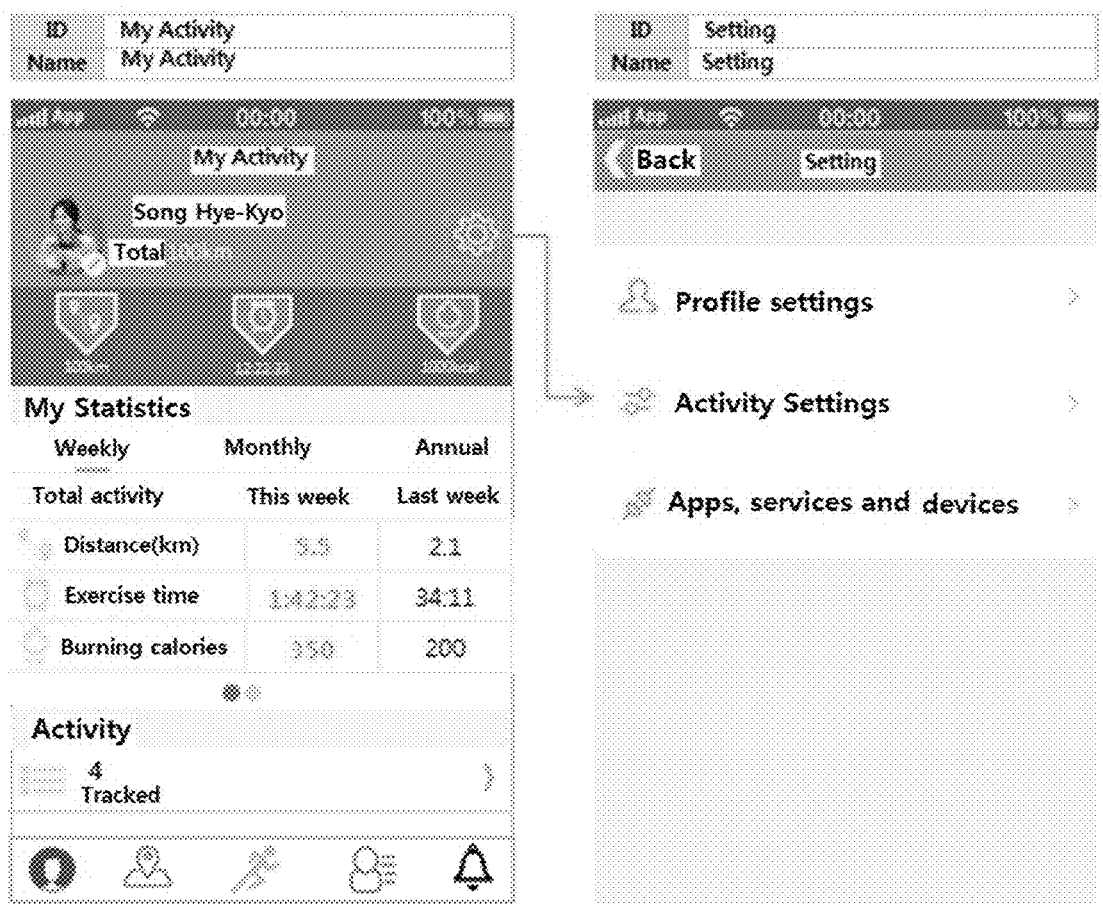

For example, a user can access a monitoring system by clicking on a login menu on an initial screen of the terminal 20 as illustrated in FIG. 5, or can clicks on an activity menu as illustrated in FIG. 6, thereby, being capable of checking statistics on a distance, exercise time, burned calories, and the like, and setting profile or the like.

Figure 7:
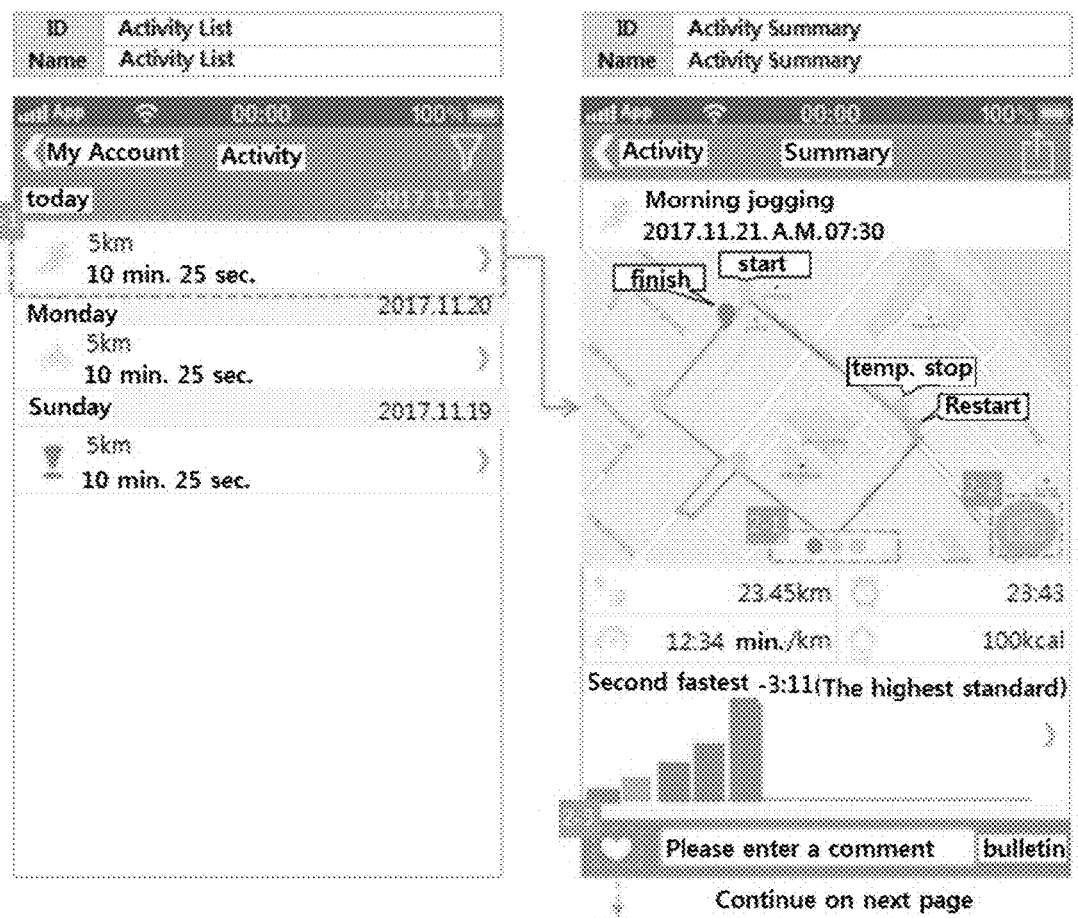

In addition, the user can confirm the results of such activities on a map as illustrated in FIG. 7.

Figure 8:

In addition, it is possible to confirm whether or not the target is reached by comparing the activity results with the existing record and to display the activity results as a graph and numerical values as illustrated in FIG. 8.

Figure 9:

In addition, as illustrated in FIG. 9, the activity result data may be analyzed in depth and statistics may be calculated.

Figure 10:
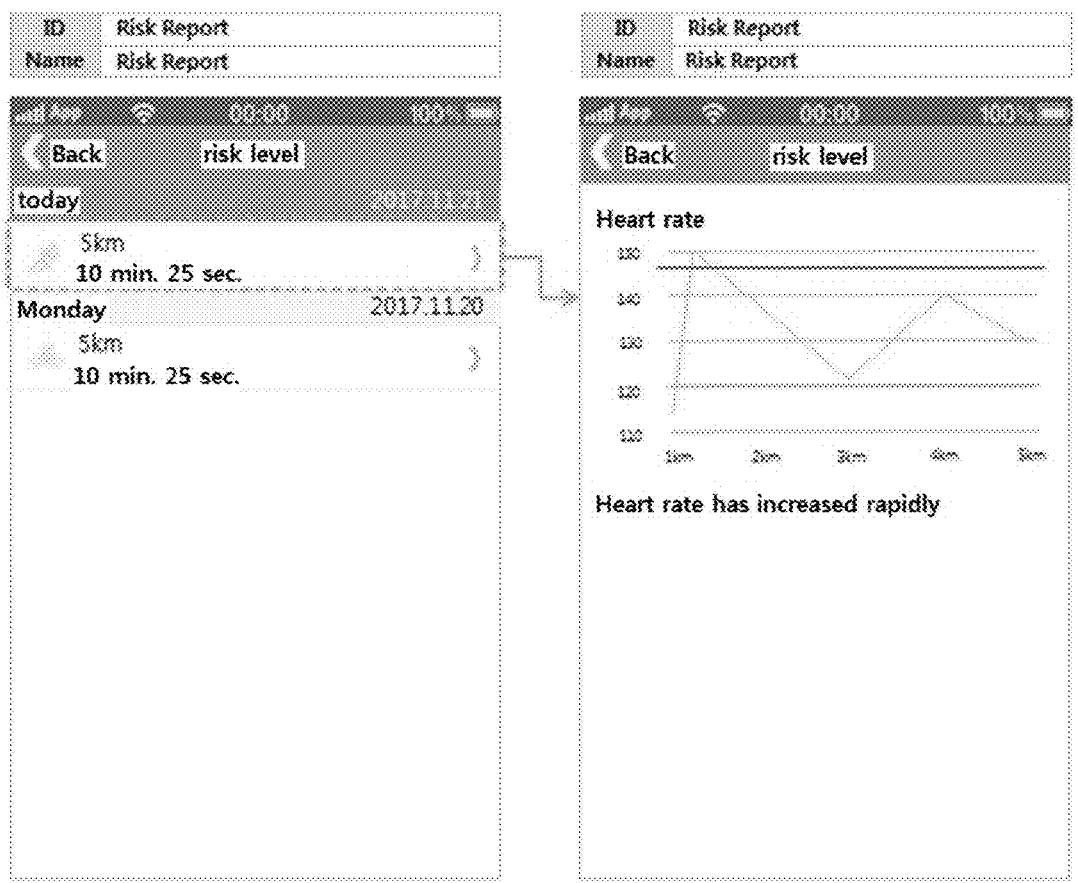

In addition, as illustrated in FIG. 10, the degree of risk of the activity results may be displayed.

Figure 11:
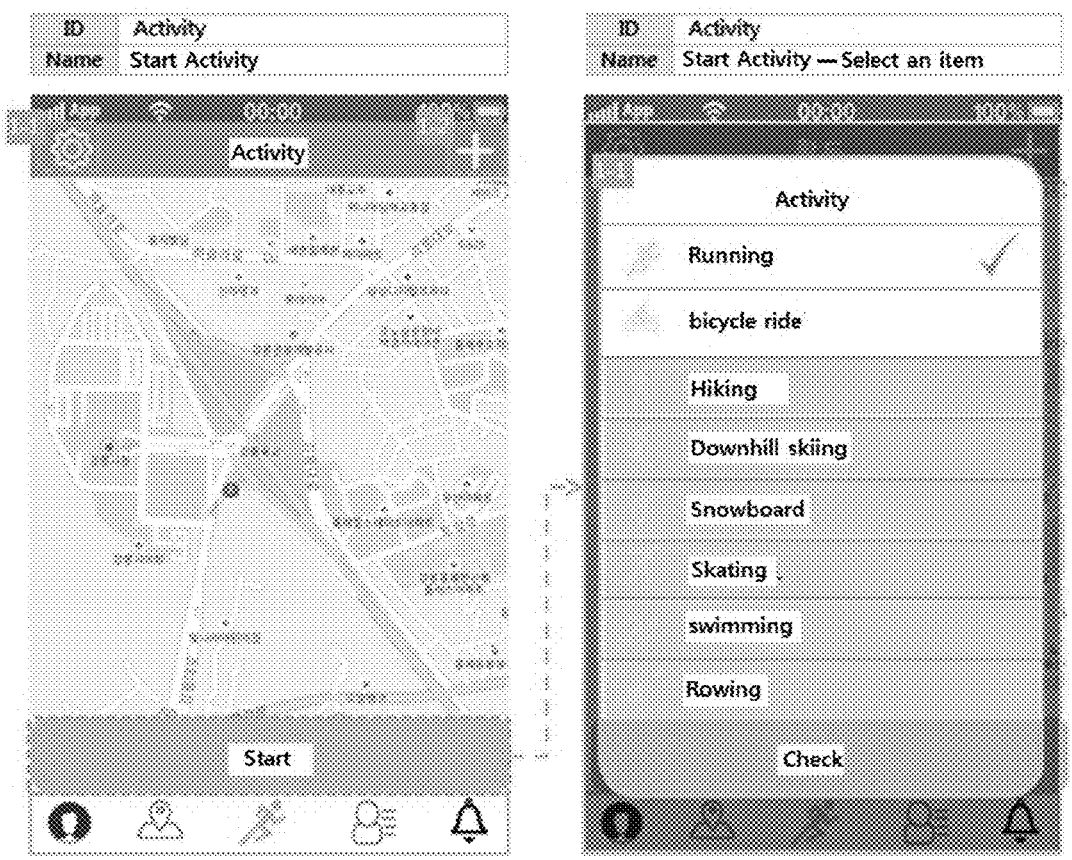

In addition, as illustrated in FIG. 11, a specific item menu for the activity may be selected, and running, cycling, hiking, and the like may be selected.

Figure 12:
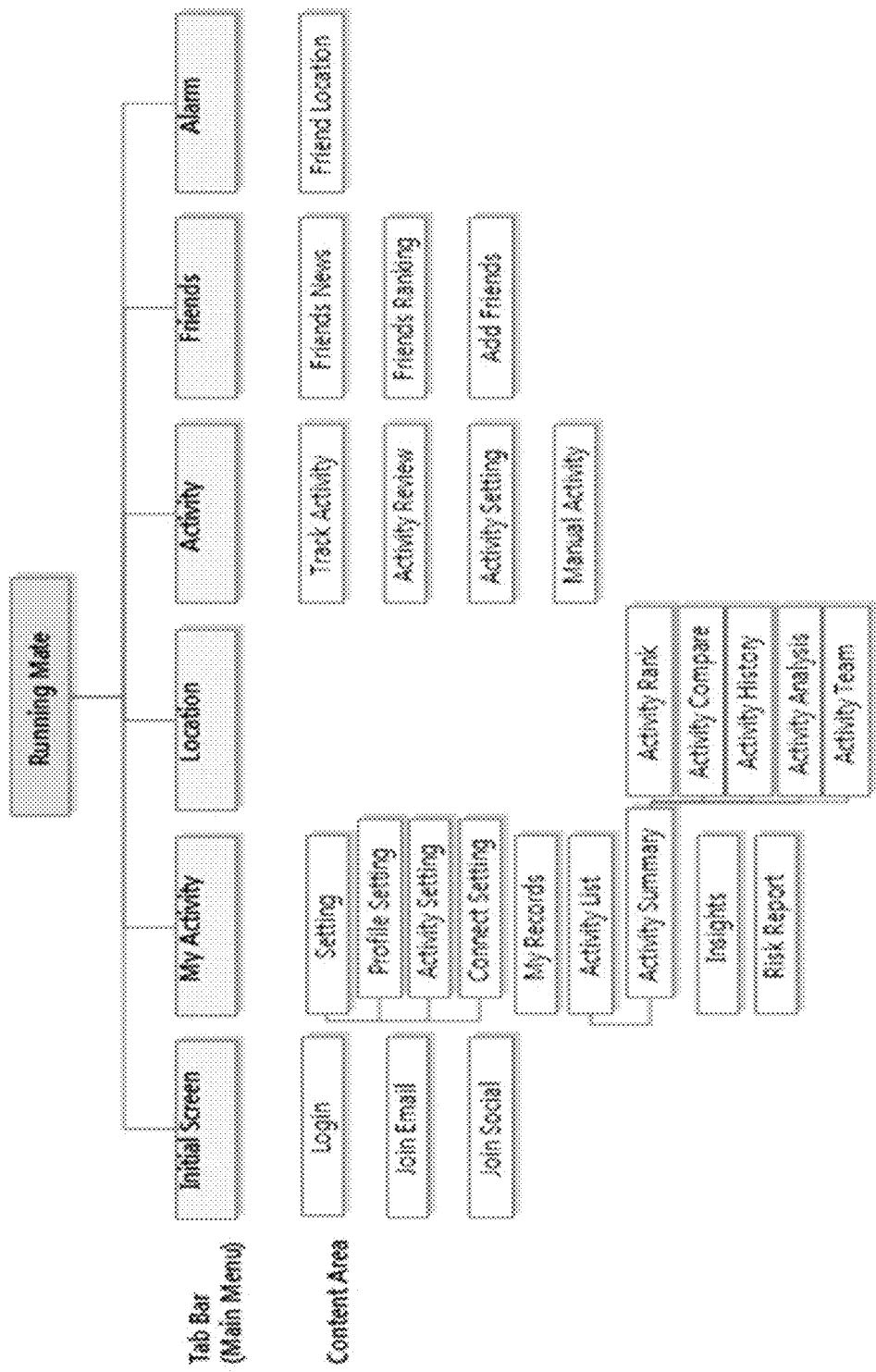

In addition, a schematic architecture for each menu of the terminal is illustrated in FIG. 12.

Meanwhile, the data processed by the terminal 20 is transmitted to the server 30, and the server 30 receives the activity information, the login information, data related to the activity type, the location information, and analyzes the data to classify activity characteristics of each user and determine whether or not an accident occurs.

The server 30 is a typical server and is connected to the terminal 20 and the wearable sensing device 10 owned by a user via a network N to manage the Internet homepage corresponding to the URL and output the Internet homepage linked to the related URL and test results in accordance with the request of the terminal 20.

In more detail, the server 30 includes a member authentication unit 32; a data collection unit 34 that classifies activity information data transmitted from the user terminal 20 into categories such as user, item, date, and type, and can store, browse, and manage the activity information data in a database 42; a data analysis unit 36 that analyzes a pattern of sports activities of a user and checks whether or not there is an accident risk in conjunction with the data collection unit 34; an artificial intelligence module 38 that processes the activity information data and related data of the user by using machine learning or an artificial neural network in conjunction with the data collection unit 34 and the data analysis unit 36; and a database 42 that stores the login information, the activity information data, the location information, and the like and outputs the data when necessary.

In the server 30 having above-described structure, the member authentication unit 32 checks whether or not the member is authenticated based on ID and password of the member to be connected and information stored in a member information DB.

At this time, the member indicates a user who wears the wearable sensing device 10 and wants to grasp his/her sports pattern.

In a case where the member logs in to the monitoring system, when the related application is activated on a screen of the terminal 20, the input window is popped up, and a member ID is input, the member may be connected.

A corresponding menu is executed when the member selects a menu. For example, the corresponding menu is executed by selecting an activity information type pattern analysis menu, a goal arrival confirmation menu, a growth rate confirmation menu, an accident risk sense menu, and the like on the screen of the terminal 20.

The data collection unit 34 classifies user activity information data transmitted from the user terminal 20 into categories such as user, item, and date, and stores the data in the respective databases 42.

The categories for each item include sports activities, such as, walking, running, cycling, skiing, snowboarding, climbing, rock climbing, rowing, and kayaking.

If a user requests the corresponding data to the terminal 20, the user may retrieve data from the database 42 and browse the data.

At this time, browsing of information on the server 30, verification of the received data, information on the server 30, analysis information, monitoring information, feedback information, and the like can be processed by the software installed in the server 30.

The activity information data processed as described above is transmitted to the data analysis unit 36, and the data analysis unit 36 synthesizes all the information collected by the wearable sensing device 10 and the terminal 20 and analyzes sports activity patterns and accident/risk patterns.

The sports activity pattern analysis is performed in a customized manner in accordance with the designated item that a user inputs through the terminal 20. That is, the pattern is analyzed by distinguishing the activity pattern in running and the activity pattern in cycle from each other.

In addition, as the activity data accumulates, the data can be classified into each level, for example, a low level, an intermediate level, a high level, and a pro. Based on the analyzed data for each level, a trend of target amounts and growth rates can be displayed separately.

For example, it is possible to grasp how much improvement in recording is achieved by comparing the initial recording at the start of running, data on running postures, and the recording and posture data at a point of time after a certain period of time elapses, with each other. In addition, it is also possible to know whether or not the running posture is changed. In addition, it is possible to classify the levels as a low level, an intermediate level, and a high level depending on the results.

In addition, the server 30 further includes an accident risk sensing module 40 to determine an accident or a dangerous state in the activity data of the user.

That is, the database 42 of the server 30 stores a reference value for variables measured by each sensor, and, when the variable is out of the reference value, it is determined to be in a dangerous state.

For example, when a user performs sports activities in a state where the wearable sensing device 10 is worn on the chest, a heartbeat of the user sensed by the heartbeat sensor 19 is transmitted to the server 30 through the terminal 20, and the server 30 monitors the heartbeat. Then, the heartbeat is compared with a reference heartbeat, and if the heartbeat is abnormally measured or the heartbeat stops in an extreme case, it can be determined to be an accident or a dangerous state.

In addition, temperature and humidity values transmitted from the temperature and humidity sensor 18 are monitored and compared with the reference value and as a result, if the values reach the dangerous state, it is determined to be an accident and dangerous state.

Alternatively, when the acceleration sensor 12 moves up and down in the Y-axis with reference to the ground, a motion vector value of the Y-axis is analyzed, and if the motion vector value is larger than the reference value, it is determined to be fallen.

At this time, a fall speed and a fall distance can be calculated by using an acceleration period and the amount of variance of time, and the patterns are stored in the database 42.

At this time, a level of an alert notification can be separately designated and operated depending on the items and levels previously designated by the user.

Then, the accident risk sensing module 40 determines the overall degree of risk by organically calculating the measurement values transmitted from the respective sensors.

For example, a rate of the heartbeat is set to 50, a rate of the acceleration value is set to 30, and a rate of the gyro sensing value is set to 10.

An equation therefor is as follows.

Degree of risk=(heartbeat×0.5)+(acceleration value×0.3)+(gyro sensing value×0.1)

Accordingly, by setting a resultant value of the heartbeat to a value higher than the acceleration and the gyro sensing value, the heartbeat is reflected most in the overall degree of risk during exercise.

As described above, an accident and a danger situation are recognized based on activity data of a user and information on the surrounding environment, the user is informed of the results through the terminal 20, a predetermined grace period of time is given to determine whether or not the user ignores the results, and if the period of time elapses, it is determined to be an accident and the assigned role is performed.

As described above, when the activity information data is accumulated and a danger level is reached, the transmitted alarm signal and the feedback result value are all reflected and are analyzed by using a machine learning technique, and thereby, the more the data is accumulated, the better accurate determination for the accurate accident/dangerous situation can be made.

In addition, the data stored in the server 20 is analyzed, the analyzed results are transmitted to the terminal 20 of a user, the user activates the application of the terminal 20, and thereby, the user can confirm an activity history, the amount of activity, trend analysis, goal value setting, and a chart on a screen.

Meanwhile, when analyzing data in the server 30, the artificial intelligence module 38 recognizes a pattern through machine learning or deep learning, corrects an error using the pattern by itself, and thereby, accuracy of sports activity data and accident risk determination gradually increases.

The artificial intelligence module 38 includes an algorithm that analyzes the activity information sensing data of the user and discriminates whether or not the user is in an accident or dangerous situation, or a physical activity for now. This can be done by calculating each measurement value transmitted from the wearable sensing device 10, for example, an acceleration value, a slope value, a magnetic force, temperature, humidity, and a heartbeat in conjunction with each other.

This allows the user to distinguish between fall, rotation, shock, high jump, immobility, exposure to cold or heat, and a normal pattern of heartbeat.

When it is determined that the user is exposed to an accident or a dangerous state as a result of the pattern analysis, the terminal 20 of the user is informed and receives feedback on whether or not the determination is correct through the application embedded in the terminal 20.

When it is determined that the user is in an accident or a dangerous state during the process, the user is automatically contacted to a contact address and an accident reception facility previously input by the user by a text message and a telephone call, and receives an alarm notification.

The above-described risk pattern analysis is performed by different criteria for each user and each item. As a result, if the user usually performs a strenuous activity, the risk determination criteria becomes higher, and of the user usually performs a normal activity, the risk determination criteria becomes lower.

In the above-described risk analysis process, a machine learning method is used, and an algorithm, which is called machine learning, is a field of artificial intelligence, and is a big data analysis technology that analyzes big data and predicts the results by making a computer to learn.

The machine learning performs a function in which patterns included in the data are found, target values are found from the large amount of data using the patterns to increase experience or accuracy, and a correct answer may be obtained by correcting an error.

In the process of analyzing the activity pattern using the machine learning, not only all the sensor values are included but also all the past and present data stored in the server 30 for monitoring activity information is referred to, and furthermore, a user discrimination value fed back when the server 30 for monitoring activity information sends an alert to the user at the time when risk occurs is additionally used.

Hereinafter, a method of monitoring a sports activity using the system will be described in detail with reference to the accompanying drawings.

As illustrated in FIGS. 1 to 12, a sports activity monitoring method proposed by the present invention includes a first step S100 in which activity information data is transmitted from the wearable sensing device 10 worn by a user; a second step S110 of inputting user information and a menu through the terminal 20, processing the transmitted activity information data, and transmitting the user information, the activity information and item information to the server 30; a third step S120 of setting an activity type, an activity history, the amount of activity, trend analysis, and a goal value by classifying the received activity information data by user, sports activity item, and period using the server 30 and performing an arithmetic operation of the data using artificial intelligence; a fourth step S130 of determining whether or not there is an accident risk by analyzing the activity information data and comparing the analyzed data with a reference value using the server 30; and a fifth step S140 of transmitting the analyzed activity state and presence or absence of the accident risk to the terminal 20 to inform the user using the server 30.

According to the monitoring method, in the first step S100, the wearable sensing device 10 is worn on the user's body such as an arm, a leg, or the chest. Accordingly, the wearable sensing device 10 measures a physical condition and an ambient condition of the user to transmit to the terminal 20.

For example, the acceleration sensor 12, the gyro sensor 14, the geomagnetic sensor 16, the temperature and humidity sensor 18, and the heartbeat sensor 19 measure a heartbeat of the user, a tilt, an acceleration, and temperature and humidity around the user, and transmit the measured values to the terminal 20 via the network.

After the first step S100 is completed, the second step is performed, and in this step, the user information and the menu are input through the terminal 20, the transmitted activity information data is processed, and thereby, the user information, the activity information, and the item information are transmitted to the server 30.

That is, the data measured by the wearable sensing device 10 is transmitted to the terminal 20 such as a smart phone, and the terminal 20 having an associated application can process the activity data and transmit the processed data to the server 30.

In more detail, the user activates the associated application installed in the terminal 20, thereby, popping up an input window on a screen to input user information. For example, the user inputs additional information on login information, his/her main sports activities, a designated activity item, location information, a sensing apparatus, and the like.

Then, the user pops up the menu on the screen of the terminal 20 and selects a relevant menu by touch or the like to execute the menu. For example, the user selects an activity information type pattern analysis menu, a goal arrival confirmation menu, a growth rate confirmation menu, an accident risk detection menu, and the like on the screen of the terminal 20, thereby, executing the relevant menu.

When the second step is completed, the third step S120 is performed. In this step, the server 30 classifies the received activity information data by user, sports activity item, and period, and performs an arithmetic operation using the artificial intelligence, thereby, setting an activity type, an activity history, the amount of activity, trend analysis, and a goal value.

That is, the server 30 classifies the data into each category depending on the types of a user, an item, date, and the like, and stores the data in each database 42.

When a user authenticates a member through the terminal 20, the user confirms whether or not the member is correct, and if the member is correct, the user is authorized to access a relevant site.

In addition, when a member selects a desired menu through the terminal 20, the menu is executed in accordance with the corresponding menu.

For example, as illustrated in FIG. 5, the user can confirm statistics on a distance, exercise time, burned calories, and the like or and can set a profile or the like by clicking on a log-in menu on an initial screen of the terminal 20 to access the corresponding monitoring system, or by clicking on the activity menu as illustrated in FIG. 6.

Moreover, activity results can be confirmed on a map as illustrated in FIG. 7.

In addition, it is possible to confirm whether or not the goal is reached by comparing the activity results with the existing record, and the comparison results can be displayed as a graph and numerical values as illustrated in FIG. 8.

In addition, as illustrated in FIG. 9, the activity result data can be analyzed in depth and the statistics can be calculated.

Then, as illustrated in FIG. 10, it is also possible to display the degree of risk of the activity results.

In addition, as illustrated in FIG. 11, a specific item menu for the activity can be selected, and running, cycling, hiking, and the like can be selected.

In this way, when the activity information type pattern analysis menu, the goal arrival confirmation menu, the growth rate confirmation menu, the accident risk detection menu, and the like are selected on the screen of the terminal 20, a procedure corresponding to each menu is performed.

For example, when the item category menu is selected, data on sports activities such as walking, running, cycling, skiing, snowboarding, mountain climbing, rock climbing, rowing, and kayaking is processed.

In addition, if a user requests the corresponding data through the terminal 20, the user can retrieve the data from the database 42 and browse the data.

If a user requests the corresponding data to the terminal 20, the user may retrieve data from the database 42 and browse the data.

At this time, browsing of information on the server 30, verification of the received data, information on the server 30, analysis information, monitoring information, feedback information, and the like can be processed by the software installed in the server 30.

The activity information data processed as described above is transmitted to the data analysis unit 36, and the data analysis unit 36 synthesizes all the information collected by the wearable sensing device 10 and the terminal 20 and analyzes sports activity patterns and accident/risk patterns.

The sports activity pattern analysis is performed in a customized manner in accordance with the designated item that a user inputs through the terminal 20. That is, the pattern is analyzed by distinguishing the activity pattern in running and the activity pattern in cycle from each other.

In addition, as the activity data accumulates, the data can be classified into each level, for example, a low level, an intermediate level, a high level, and a pro. Based on the analyzed data for each level, a trend of target amounts and growth rates can be displayed separately.

In this way, if the third step S120 is completed, the fourth step S130 is performed, and in this step, the server 30 analyzes the activity information data and compares the activity information data with a reference value, thereby, determining whether or not there is an accident risk.

That is, the sensed value is compared with a reference value for the variables measured by each sensor stored in the database 42 by linking the accident risk detection module 40 and the database 42 of the server 30 to each other, and if the sensed value is out of the reference value, it is determined to be in a dangerous state.

For example, when a user performs sports activities in a state where the wearable sensing device 10 is worn on the chest, a heartbeat of the user sensed by the heartbeat sensor 19 is transmitted to the server 30 through the terminal 20, and the server 30 monitors the heartbeat. Then, the heartbeat is compared with a reference heartbeat, and if the heartbeat is abnormally measured or the heartbeat stops in an extreme case, it can be determined to be an accident or a dangerous state.

In addition, temperature and humidity values transmitted from the temperature and humidity sensor 18 are monitored and compared with the reference value and as a result, if the values reach the dangerous state, it is determined to be an accident and dangerous state.

Alternatively, when the acceleration sensor 12 moves up and down in the Y-axis with reference to the ground, a motion vector value of the Y-axis is analyzed, and if the motion vector value is larger than the reference value, it is determined to be fallen.

At this time, a fall speed and a fall distance can be calculated by using an acceleration period and the amount of variance of time, and the patterns are stored in the database 42.

At this time, a level of an alert notification can be separately designated and operated depending on the items and levels previously designated by the user.

When the accident risk is determined, the accident risk sensing module 40 determines the overall degree of risk by organically calculating the measurement values transmitted from the respective sensors.

For example, a rate of the heartbeat is set to 50, a rate of the acceleration value is set to 30, and a rate of the gyro sensing value is set to 10.

An equation therefor is as follows.

$$\text{Degree of risk} = (\text{heartbeat} \times 0.5) + (\text{acceleration value} \times 0.3) + (\text{gyro sensing value} \times 0.1)$$

Accordingly, by setting a resultant value of the heartbeat to a value higher than the acceleration and the gyro sensing value, the heartbeat is reflected most in the overall degree of risk during exercise.

As described above, an accident and a danger situation are recognized based on activity data of a user and information on the surrounding environment, the user is informed of the results through the terminal 20, a predetermined grace period of time is given to determine whether or not the user ignores the results, and if the period of time elapses, it is determined to be an accident and the assigned role is performed.

As described above, when the activity information data is accumulated and a danger level is reached, the transmitted alarm signal and the feedback result value are all reflected and are analyzed by using a machine learning technique, and thereby, the more the data is accumulated, the better accurate determination for the accurate accident/dangerous situation can be made.

In addition, the data stored in the server 20 is analyzed, the analyzed results are transmitted to the terminal 20 of a user, the user activates the application of the terminal 20, and thereby, the user can confirm an activity history, the amount of activity, trend analysis, goal value setting, and a chart on a screen.

In the fifth step S140, the activity state and presence or absence of the accident risk is transmitted to the terminal 20 to inform the user using the server 30.

When it is determined that the user is in an accident or a dangerous state as an analysis result of the server 30, the user is automatically contacted to a contact address and an accident reception facility previously input by the user by a text message and a telephone call, and receives an alarm notification.

The invention claimed is:

1. A sports activity monitoring system comprising:
   a wearable sensing device that is as worn by a user and is capable of sensing an activity state of the user;
   a terminal capable of processing activity information data of the user in conjunction with the wearable sensing device; and
   a server that is connected to the terminal through a network, grasps a sports activity pattern, personal data of the user for a sports event, and whether or not an accident occurs by receiving, processing, and analyzing the activity information data of the user, and transmits grasped result data to the terminal, wherein the server includes:
   a member authentication unit;
   a data collection unit that classifies activity information data which is transmitted from the terminal of the user into categories, and is able to store, browse, and manage the activity information data in a database;
   a data analysis unit that analyzes a pattern of sports activity of the user and checks whether or not there is an accident risk in conjunction with the data collection unit;
   an artificial intelligence module that processes the activity information data of the user by using machine learning or an artificial neural network in conjunction with the data collection unit and the data analysis unit; and
   the database that stores login information, the activity information data, location information.

2. The sports activity monitoring system according to claim 1, wherein the wearable sensing device includes at least one of an acceleration sensor, a gyro sensor, a geomagnetic sensor, a temperature and humidity sensor, and a heartbeat sensor.

3. The sports activity monitoring system according to claim 1, wherein the terminal includes
   a data processing unit that converts real-time activity data, user information, user location information, user history information, and a sensing period of the wearable sensing device which are received from the wearable sensing device into a predetermined protocol form, filters the converted data, and transmits the filtered data to the server;
   a control unit that processes a command which is input by the user through a screen of the terminal in conjunction with the data processing unit, or receives or transmits data from or to the wearable sensing device and the server; and
   an output unit that transmits the data which is processed by the data processing unit to each electronic element in the terminal or transmits the data to the server.

4. The sports activity monitoring system according to claim 1, wherein the server further includes an accident risk detection module that is able to determine an accident or a dangerous state in the activity data of the user, compares a sensed value which is measured by the wearable sensing device with a reference value in the database, and determines that the user is in a dangerous state, when the sensed value is out of the reference value.

5. The sports activity monitoring system according to claim 4, wherein, when determining whether or not the user is in an accident risk, determining is made by an equation which is degree of risk=(heartbeat×0.5)+(acceleration value×0.3)+(gyro sensing value×0.1).

* * * * *